(12) United States Patent
Ilagan et al.

(10) Patent No.: US 11,571,444 B2
(45) Date of Patent: Feb. 7, 2023

(54) ENHANCEMENT OF MSC IMMUNOMODULATORY PROPERTIES BY TREPROSTINIL

(71) Applicant: United Therapeutics Corporation, Silver Spring, MD (US)

(72) Inventors: Roger Marquez Ilagan, Durham, NC (US); Sarah Hogan, Raleigh, NC (US); John B. Cheadle, Durham, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 245 days.

(21) Appl. No.: 15/790,666

(22) Filed: Oct. 23, 2017

(65) Prior Publication Data

US 2018/0110807 A1    Apr. 26, 2018

Related U.S. Application Data

(60) Provisional application No. 62/411,950, filed on Oct. 24, 2016.

(51) Int. Cl.
*A61K 35/28* (2015.01)
*A61K 31/192* (2006.01)
*C12N 5/0775* (2010.01)

(52) U.S. Cl.
CPC ............ *A61K 35/28* (2013.01); *A61K 31/192* (2013.01); *C12N 5/0663* (2013.01); *C12N 2501/02* (2013.01)

(58) Field of Classification Search
CPC ...... A61K 35/28; A61K 31/192; C12N 5/0663
See application file for complete search history.

(56) References Cited

U.S. PATENT DOCUMENTS

| | | |
|---|---|---|
| 3,089,815 A | 5/1963 | Lieb et al. |
| 4,352,883 A | 10/1982 | Lim |
| 4,353,888 A | 10/1982 | Sefton |
| 4,714,680 A | 12/1987 | Civin |
| 4,965,204 A | 10/1990 | Civin |
| 4,968,733 A | 11/1990 | Mueller et al. |
| 4,976,859 A | 12/1990 | Wechs |
| 4,983,393 A | 1/1991 | Cohen et al. |
| 5,026,365 A | 6/1991 | Rossini et al. |
| 5,035,994 A | 7/1991 | Civin |
| 5,071,741 A | 12/1991 | Brockbank |
| 5,084,350 A | 1/1992 | Chang et al. |
| 5,130,144 A | 7/1992 | Civin |
| 5,137,809 A | 8/1992 | Loken et al. |
| 5,158,881 A | 10/1992 | Aebischer et al. |
| 5,284,761 A | 2/1994 | Aebischer et al. |
| 5,643,192 A | 7/1997 | Hirsh et al. |
| 5,651,982 A | 7/1997 | Marx |
| 5,691,176 A | 11/1997 | Lebkowski et al. |
| 5,693,531 A | 12/1997 | Chiorini et al. |
| 5,750,397 A | 5/1998 | Tsukamoto et al. |
| 5,800,828 A | 9/1998 | Dionne et al. |
| 5,811,094 A | 9/1998 | Caplan et al. |
| 6,387,369 B1 | 5/2002 | Pittenger et al. |
| 6,468,527 B2 | 10/2002 | Austin et al. |
| 7,638,128 B2 | 12/2009 | Dzau et al. |
| 10,071,123 B2 * | 9/2018 | Jeffs ...................... A61K 45/06 |
| 10,080,730 B2 * | 9/2018 | Jeffs .................... A61K 31/192 |
| 2003/0118567 A1 | 6/2003 | Stewart |
| 2005/0165111 A1 | 7/2005 | Wade et al. |
| 2007/0065414 A1 | 3/2007 | Freyman et al. |
| 2008/0050349 A1 | 2/2008 | Stewart |
| 2008/0226595 A1 | 9/2008 | Edinger et al. |
| 2009/0177262 A1 | 7/2009 | Oberti et al. |
| 2009/0274665 A1 | 11/2009 | Akabutu et al. |
| 2010/0040584 A1 | 2/2010 | Melero-Martin et al. |
| 2011/0003008 A1 | 1/2011 | Lim |
| 2012/0172970 A1 | 7/2012 | Cottone, Jr. et al. |
| 2014/0193379 A1 | 7/2014 | Jeffs et al. |
| 2014/0234278 A1 | 8/2014 | Heffner et al. |
| 2015/0216909 A1 | 8/2015 | Jeffs et al. |
| 2015/0246078 A1 | 9/2015 | Jeffs et al. |

FOREIGN PATENT DOCUMENTS

| | | |
|---|---|---|
| WO | WO 92/04033 A1 | 3/1992 |
| WO | WO 92/19195 A1 | 11/1992 |
| WO | WO 93/14191 A1 | 7/1993 |
| WO | WO 94/29438 A1 | 12/1994 |
| WO | WO 95/05452 A1 | 2/1995 |
| WO | WO 95/07611 A1 | 3/1995 |
| WO | WO 95/27071 A1 | 10/1995 |
| WO | WO 96/27287 A1 | 9/1996 |
| WO | WO 96/29862 A1 | 10/1996 |
| WO | WO 97/21824 A1 | 6/1997 |
| WO | WO 97/21825 A1 | 6/1997 |
| WO | WO 98/14058 A1 | 4/1998 |
| WO | WO 98/20027 A2 | 5/1998 |
| WO | WO 2000/024897 A1 | 5/2000 |
| WO | WO 01/04268 A1 | 1/2001 |
| WO | WO 2004/050180 A2 | 6/2004 |
| WO | WO 2004/084921 A1 | 10/2004 |
| WO | WO 2004/085630 A1 | 10/2004 |
| WO | WO 2006/032092 A1 | 3/2006 |
| WO | WO 2009/057313 A1 | 5/2009 |
| WO | WO 2009/105044 A1 | 8/2009 |
| WO | WO 2012/027740 A1 | 3/2012 |
| WO | WO 2014/022373 A1 | 2/2014 |
| WO | WO 2014/022376 A2 | 2/2014 |

OTHER PUBLICATIONS

Clinical All-Round, Nov. 2009, 58(11):2324-2337.
Kawabe, Junichi, "Q&A about Thrombosis (Part 6): Please explain prostacyclin and revascularization," Thrombosis and Circulation, 2011, 19(1):189-191.
Lai et al., "Exosome secreted by MSC reduces myocardial ischemia/reperfusion injury," Stem Cell Research, 2010, 4(3):214-222.

(Continued)

*Primary Examiner* — Laura Schuberg
(74) *Attorney, Agent, or Firm* — Foley & Lardner LLP

(57) ABSTRACT

Provided are methods for treating or preventing vasculopathy comprising administering to a subject in need thereof, ac composition comprising a mesenchymal stem cell (MSC), or a part of a culture medium that has been in contact with the MSC and comprises one or more components of the MSC, or an exosome derived from the MSC. Pharmaceutical compositions suitable for such treatment is also provided.

16 Claims, 7 Drawing Sheets

(56) References Cited

OTHER PUBLICATIONS

Lai et al., "Mesenchymal stem cell exosome: a novel stem cell-based therapy for cardiovascular disease," Regen. Med., 2011, 6(4):481-492.
Abisambra et al., "Abstracts for the 19th Annual Meeting of the American Society for Neural Therapy and Repair," Cell Transplantation, 2012, 21:773-797.
Aizman et al., "Extracellular Matrix Produced by Bone Marrow Stromal Cells and by Their Derivative, SB623 Cells, Supports Neural Cell Growth," Journal of Neuroscience Research, 2009, 87:3198-3206.
"Second European Consensus Document on Chronic Critical Leg Ischemia", Circulation, Nov. 1991, 84(4 Suppl.):IV-1-IV-26.
Actelion Pharmaceuticals, "VELETRI: epoprostenol," prescribing information, 2011, 4 pages.
Allen et al., "Type I collagen, fibrin and PuraMatrix matrices provide permissive environments for human endothelial and mesenchymal progenitor cells to form neovascular networks," Journal of Tissue Engineering and Regenerative Medicine, 2011, 5:e74-e86.
Asahara et al., "Isolation of Putative Progenitor Endothelial Cells for Angiogenesis," Science, Feb. 17, 1997, 275:964-967.
Assmus et al., "Transplantation of Progenitor Cells and Regeneration Enhancement in Acute Myocardial Infarction (TOPCARE-AMI)," Circulation, Nov. 11, 2002, 106:3009-3017.
Barst, Robyn MD, FACC, "Is it Possible to Reverse the Endothelial Dysfunction in Pulmonary Arterial Hypertension?", Journal of the American College of Cardiology, 2007, 49(14):1572-1574.
Bregni et al., "Human Peripheral Blood Hematopoietic Progenitors Are Optimal Targets of Retroviral-Mediated Gene Transfer," Blood, Sep. 15, 1992, 80(6):1418-1422.
Chen et al., "Effect on Left Ventricular Function of Intracoronary Transplantation of Autologous Bone Marrow Mesenchymal Stem Cell in Patients with Acute Myocardial Infarction," The American Journal of Cardiology, Jul. 1, 2004, 94:92-95.
Coffin et al., Eds. "Retroviruses", Chapter 9 pp. 437-473, Cold Springs Harbor Laboratory Press, 1997.
D'Alonzo et al., "Survival in Patients with Primary Pulmonary Hypertension," Ann. Intern. Med., Sep. 1, 1991, 115(5):343-349.
Das et al., "The Role of Hypoxia in Bone Marrow-Derived Mesenchymal Stem Cells: Considerations for Regenerative Medicine Approaches," Tissue Engineering: Part B, Apr. 1, 2010, 16(2):159-168.
Di Stefano et al., "The prostacyclin analogue iloprost increases circulating endothelial progenitor cells in patients with critical limb ischemia," Thrombosis and Haemostasis, Oct. 13, 2008, 100(5):871-877.
Doyle et al., "Endothelial Progenitor Cells," Endothelium, 2006, 13(6):403-410.
Eells et al., "Advances in Prostacyclin Therapy for Pulmonary Arterial Hypertension," Critical Care Nurse, Apr. 2004, 24(2):42-54.
Eneroth et al., "Amputation for occlusive arterial disease, a prospective multicentre study of 177 amputees," Int. Orthop. (SICOT), 1992, 16:383-387.
Flamme et al., "Induction of vasculogenesis and hematopoiesis in vitro," Development, 1992, 116(2):435-439.
Grant et al., "Iloprost: a Review of its Pharmacodynamic and Pharmacokinetic Properties, and Therapeutic Potential in Peripheral Vascular Disease, Myocardial Ischaemia and Extracorporeal Circulation Procedures," Drugs, 1992, 43(6):889-924.
Gruber, Scott A., "The Case for Local Immunosuppression," Transplantation, Jul. 1992, 54:1-11.
Hall et al., "Endothelin receptor expression in idiopathic pulmonary arterial hypertension: effect of bosentan and epoprostenol treatment," Eur. Respir. J., 2011, 38:851-860.
Hatzopoulos et al., "Isolation and characterization of endothelial progenitor cells from mouse embryos," Development, 1998, 125(8):1457-1468.
He et al., "Angiogenic function of prostacyclin biosynthesis in human endothelial progenitor cells," Circulation Research, Jul. 3, 2008, 103(1):80-88.
Hill et al., "Circulating Endothelial Progenitor Cells, Vascular Function, and Cardiovascular Risk," N. Engl. J. Med., 2003, 348:593-600.
Hu et al., "Exosomal miRNAs: biological properties and therapeutic potential," Frontiers in Genetics, Apr. 20, 2012, 3(56):1-9.
Humbert et al., "Cellular and Molecular Pathobiology of Pulmonary Arterial Hypertension," J. Am. Coll. Cardiol., 2004, 43(12:SupplS):13S-24S.
Ingram et al., "Identification of a novel hierarchy of endothelial progenitor cells using human peripheral and umbilical cord blood," Blood, Jun. 29, 2004, 104:2752-2760.
Ishii et al., "Mesenchymal stem cell-based gene therapy with prostacyclin synthase enhanced neovascularization in hindlimb ischemia," Atherosclerosis, 2009, 206:109-118.
Isner et al., "Angiogenesis and vasculogenesis as therapeutic strategies for postnatal neovascularization," J. Clin. Invest., May 1999, 103(9):1231-1236.
Kalka et al., "Transplantation of ex vivo expanded endothelial progenitor cells for therapeutic neovascularization," P.N.A.S., Mar. 29, 2000, 97(7):3422-3427.
Kamio et al., "Prostacyclin analogs stimulate VEGF production from human lung fibroblasts in culture," Am. J. Physiol. Lung Cell. Mol. Physiol., 2008, 294:L1226-L1232.
Karlsson et al., "Nucleation and Growth of Ice Crystals Inside Cultured Hepatocytes During Freezing in the Presence of Dimethyl Sulfoxide," Biophysical J., Dec. 1993, 65:2524-2536.
Kawabe et al., "Role of Autocrine Prostacyclin System in Crucial Functions of Endothelial Progenitor Cells," Circ. J., 2008, 72(Suppl. 1):503, PE-570.
Keeley et al., "Fibrocytes: Bringing new insights into mechanisms of inflammation and fibrosis," Int. J. Biochem. Cell Biol., 2010, 42:535-542.
Kuo et al., "Effect of Prostaglandin $I_2$ Analogs on Cytokine Expression in Human Myeloid Dendritic Cells via Epigenetic Regulation," Molecular Medicine, 2012, 18:433-444.
Lau et al., "Stem Cells and Regenerative Medicine in Lung Biology and Diseases," Molecular Therapy, Mar. 6, 2012, 20(6):1116-1130.
Lee et al., "Exosomes Mediate the Cytoprotective Action of Mesenchymal Stromal Cells on Hypoxia-Induced Pulmonary Hypertension," Circulation, Oct. 31, 2012, 126(22):2601-2611.
Liu et al., "Engineered Endothelial Progenitor Cells That Overexpress Prostacyclin Protect Vascular Cells," Journal of Cellular Physiology, Mar. 20, 2012, 227(7):2907-2916.
Mayer et al., "Vascular Endothelial Growth Factor (VEGF-A) Expression in Human Mesenchymal Stem Cells: Autocrine and Paracrine Role on Osteoblastic and Endothelial Differentiation," Journal of Cellular Biochemistry, Jul. 1, 2005, 95(4):827-839.
Murohara et al., "Transplanted cord blood-derived endothelial precursor cells augment postnatal neovascularization," J. Clin. Invest., Jun. 2000, 105(11):1527-1536.
Nagaya et al., "Hybrid Cell-Gene Therapy for Pulmonary Hypertension Based on Phagocytosing Action of Endothelial Progenitor Cells," Circulation, Jun. 30, 2003, 108:889-895.
Ribatti, Domenico, "The discovery of endothelial progenitor cells, an historical review," Leukemia Research, 2007, 31:439-444.
Risau et al., "Vasculogenesis and angiogenesis in embryonic-stem-cell-derived embryoid bodies," Development, 1988, 102(3):471-478.
Risau, Werner, "Differentiation of endothelium," FASEB J., 1995, 9(10):926-933.
Risau, Werner, "Mechanisms of angiogenesis," Nature, Apr. 17, 1997, 386(6626):671-674.
Rissanen et al., "Gene therapy for therapeutic angiogenesis in critically ischaemic lower limb—on the way to the clinic," European Journal of Clinical Investigation, 2001, 31:651-666.
Ruan et al., "Prostacyclin Therapy for Pulmonary Arterial Hypertension," Texas Heart Institute Journal, 2010, 37(4):391-399.
Sahara, Makoto, Clinic All-Round, 2009, 58(11):2324-2336, with English translation of indicated relevant portions.

(56) References Cited

OTHER PUBLICATIONS

Shantsila et al., "Endothelial Progenitor Cells in Cardiovascular Disorders," Journal of the American College of Cardiology, 2007, 49(7):741-752.

Shintani, Satoshi, Heart View, 2011, 15(8):90-96, with English translation of indicated relevant portions.

Smadja et al., "Treprostinil increases the number and angiogenic potential of endothelial progenitor cells in children with pulmonary hypertension," Angiogenesis, 2011, 14(1):17-27.

Smithies et al., "Insertion of DNA sequences into the human chromosomal Beta-globin locus by homologous recombination," Nature, Sep. 19, 1985, 317:230-234.

Takahashi et al., "Ischemia- and cytokine-induced mobilization of bone marrow-derived endothelial progenitor cells for neovascularization," Nature Medicine, Apr. 1999, 5(4):434-438.

Topol et al., "Combined Tissue-Type Plasminogen Activator and Prostacyclin Therapy for Acute Myocardial Infarction," J. Am. Coll. Cardiol., 1989, 14(4):877-884.

Tyrrell et al., "Critical leg ischaemia: an appraisal of clinical definitions," Br. J. Surg., Feb. 1003, 80:177-180, 1993.

Umar et al., "Novel Approaches to Treat Experimental Pulmonary Arterial Hypertension: a Review," Journal of Biomedicine and Biotechnology, Jan. 1, 2010, 8(1):1-11, Article ID 702836.

Wang et al., "Transplantation of Autologous Endothelial Progenitor Cells May Be Beneficial in Patients With Idiopathic Pulmonary Arterial Hypertension," J. Am. Coll. Cardiol., 2007, 49(14):1566-1571.

Williams et al., "Mesenchymal Stem Cells: Biology, Pathophysiology, Translational Findings, and Therapeutic Implications for Cardiac Disease," Circ. Res., 2011, 109:923-940.

Yoder et al., "Redefining endothelial progenitor cells via clonal analysis and hematopoietic stem/progenitor cell principals," Blood, 2007, 109:1801-1809.

Zhao et al., "Rescue of Monocrotaline-Induced Pulmonary Arterial Hypertension Using Bone Marrow-Derived Endothelial-Like Progenitor Cells," Circ. Res., 2006, 96:442-450.

Zhen et al., "Mesenchymal stem cell transplantation increases expression of vascular endothelial growth factor in papain-induced emphysematous lungs and inhibits apoptosis of lung cells," Cytotherapy, Sep. 1, 2010, 12(5):605-614.

Zheng et al., "Fidelity of targeted recombination in human fibroblasts and murine embryonic stem cells," Proc. Natl. Acad. Sci. USA, Sep. 1991, 88:8067-8071.

Boeing et al.,. "Single-step isolation of extracellular vesicles by size-exclusion chromatography," Journal of Extracellular Vesicles, Sep. 8, 2014, 3:1:23430.

Dominici et al., "Minimal criteria for defining multipotent mesenchymal stromal cells. The International Society fo Cellular Therapy position statement," Cytotherapy, 2006, 8(4):315-317.

Dormandy et al., "Chronic Critical Limb Ischemia," J. Vase. Surg. 2000, 31:S168-S175.

Groth et al., "Inflammatory cytokines in pulmonary hypertension," Respiratory Research, 2014, 15:47.

Hoogduijn et al., "The immunomodulatory properties of mesenchymal stem cells and their use for immunotherapy," International Immunopharmacology, 2010, 10:1496-1500.

Hu et al., "Exosomal miRNAs: biological properties and therapeutic potential," Frontiers in Genetics, 2012, 3(56):1-9.

Keily et al., "Pulmonary hypertension: diagnosis and management," BMJ, 2013, 346:f2028, 1-12.

Thery et al., "Isolation and Characterization of Exosomes from Cell Culture Supernatants and Biological Fluids," Current Protocols in Cell Biol., 2006, 3.22.1-3.22.29.

Tyrrell et al., "Critical leg ischaemia: an appraisal of clinical definitions," Br. J. Surg., Feb. 1993, 80:177-180.

\* cited by examiner

ENHANCEMENT OF MSC IMMUNOMODULATORY PROPERTIES BY TREPROSTINIL

CROSS REFERENCE TO RELATED APPLICATIONS

This application claims priority to U.S. Provisional Patent Application No. 62/411,950 filed Oct. 24, 2016, which is hereby incorporated by reference in its entirety.

BACKGROUND

The present application relates to mesenchymal stem cells with anti-inflammatory properties, method of making such mesenchymal stem cells, materials obtained from such mesenchymal stem cells, the use of mesenchymal stem cells and materials obtained from mesenchymal stem cells in treatment of vasculopathy. Vasculopathy includes, but is not limited to, pulmonary arterial hypertension (PAH), other types of pulmonary hypertension, peripheral vascular disease (PVD), critical limb ischemia (CLI), coronary artery disease, and diabetic vasculopathy.

Pulmonary hypertension is a rare, progressive, and life-threatening disease affecting the pulmonary vasculature. Specifically, pulmonary hypertension results in increased pressure in the pulmonary vasculature, which can lead to heart failure among other outcomes. Currently, pulmonary hypertension is classified into the following groups under the World Health Organisation (WHO) clinical classification system (Dana Point 2008):
Group 1: Pulmonary arterial hypertension (PAH);
Group 1': Pulmonary veno-occlusive disease (PVOD) and/or pulmonary capillary haemangiomatosis (PCH);
Group 2: Pulmonary hypertension due to left heart diseases;
Group 3: Pulmonary hypertension due to lung diseases and/or hypoxemia;
Group 4: Chronic thromboembolic pulmonary hypertension (CTEPH); and
Group 5: PH with unclear multifactorial mechanisms.

Pulmonary arterial hypertension is a specific type of pulmonary hypertension and, untreated, leads to death on average within 2.8 to 5 years after being diagnosed (Keily et al. (2013) *BMJ* 346:f2028). An increasing constriction of the pulmonary circulation leads to increased stress on the right heart, which may develop into right heart failure. By definition, the mean pulmonary arterial pressure (mPAP) in a case of chronic pulmonary hypertension is>25 mmHg at rest or>30 mmHg during exertion (normal value<20 mmHg). The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This resulting increase in pulmonary arterial pressures results in progressive stress on the right heart, which leads to a reduced output from the right heart and eventually ends in right heart failure (M. Humbert et al., *J Am. Coll. Cardiol.* 2004, 43, 13S-24S). PAH is a rare disorder, with a prevalence of 1-2 per million. The average age of the patients has been estimated to be 36 years, and only 10% of the patients were over 60 years of age. Distinctly more women than men are affected (G. E. D'Alonzo et al., *Ann. Intern. Med.* 1991, 115, 343-349).

Standard therapies available on the market (e.g., prostacyclin analogues, endothelin receptor antagonists, phosphodiesterase inhibitors) are able to improve the quality of life and the exercise tolerance of patients. These medicaments can result in serious side effects and/or must be delivered using complicated types of administration. Patients are frequently on combination therapy, either at the outset or after a deterioration in condition following monotherapy. Despite the advances in treatment, there is no cure for PAH.

Thus, a need exists to develop improved therapeutic compositions and methods for treating vasculopathy, including PAH.

SUMMARY

In one aspect, the present disclosure provides a method of treating or preventing vasculopathy, comprising administering to a subject in need thereof a composition comprising (i) a mesenchymal stem cell (MSC), or (ii) a part of a culture medium that has been in contact with the MSC and comprises one or more components of the MSC, or (iii) an exosome derived from the MSC, wherein the MSC has been exposed ex vivo to a prostacyclin, and wherein the exposure to the prostacyclin increases the expression of one or more anti-inflammatory factors and/or reduces the expression of one or more pro-inflammatory factors in the MSC, compared to a control MSC not exposed to the prostacyclin.

In some embodiments, prior to the administration, the MSC is exposed to 0.3 µg/mL to 83.3 µg/mL of prostacyclin. In other embodiments, prior to the administration, the MSC is exposed to 0.3 µg/mL to 10 µg/mL of prostacyclin.

In some embodiments, the prostacyclin is treprostinil, a derivative or a pharmaceutically acceptable salt thereof.

In some embodiments, the MSC is exposed to the prostacyclin for at least 24 hours. In other embodiments, the MSC is exposed to the prostacyclin for at least 48 hours.

In some embodiments, the vasculopathy being treated is selected from the group consisting of pulmonary arterial hypertension (PAH), peripheral vascular disease (PVD), critical limb ischemia (CLI), coronary artery disease and diabetic vasculopathy.

In some embodiments, the MSC is exposed to the prostacyclin post-expansion.

In some embodiments, the MSC exposed to the prostacyclin has a reduced expression level of tumor necrosis factor alpha (TNFα), compared to a control MSC not exposed to the prostacyclin. In some embodiments, the MSC exposed to the prostacyclin has a reduced expression level of Interleukin-4 (IL-4), compared to a control MSC not exposed to the prostacyclin.

In other embodiments, the MSC exposed to the prostacyclin has an increased expression level of one or more anti-inflammatory factors selected from the group consisting of IL10, IL13, IDO, iNOS, HLA and TGFβ, compared to a control MSC not exposed to the prostacyclin.

In some embodiments, the MSC exposed to the prostacyclin has an expression level of TNFα that is at least 50% lower than that of a control MSC not exposed to the prostacyclin. In other embodiments, the MSC exposed to the prostacyclin has an expression level of at least one of IL10, IL13, IDO, iNOS, HLA and TGFβ that is at least 50% higher than that of a control MSC not exposed to the prostacyclin.

In some embodiments, the method of the present invention comprises administering to a subject in need thereof a composition comprising a MSC, wherein the MSC has been exposed ex vivo to treprostinil or a pharmaceutically acceptable salt thereof at a concentration of 0.3 to 10 µg/mL for at least 24 hours.

In some embodiments, the method of the present invention comprises administering to the subject a composition comprising a part of a culture medium that has been in contact with the MSC and comprises one or more components of the MSC, wherein the MSC has been exposed ex vivo to treprostinil or a pharmaceutically acceptable salt thereof at a concentration of 0.3 to 10 µg/mL for at least 24 hours, and wherein the one or more components of the MSC are selected from the group consisting of an exosome, a microvesicle, a microRNA, a messenger RNA, a non-coding RNA, a mitochondria, a growth factor, and the combinations thereof.

In some embodiments, the method of the present invention comprises administering to a subject in need thereof a composition comprising an exosome derived from the MSC, wherein the MSC has been exposed ex vivo to treprostinil or a pharmaceutically acceptable salt thereof at a concentration of 0.3 to 10 µg/mL for at least 24 hours.

In some embodiments, the MSC is exposed to treprostinil or a pharmaceutically acceptable salt thereof having a concentration of 0.3 µg/mL to 10 µg/mL for at least 24 hours.

Also provided is a method for preparing a composition comprising a mesenchymal stem cell (MSC) or a culture medium that has been in contact with the MSC and comprises one or more components of the MSC, comprising exposing the MSC ex vivo to a prostacyclin, and wherein the exposure to the prostacyclin increases the expression of one or more anti-inflammatory factors and/or reduces the expression of one or more pro-inflammatory factors in the MSC, compared to a control MSC not exposed to the prostacyclin; and isolating the MSC or the culture medium or the one or more components of the MSC.

In some embodiments, the method comprises treating the MSC with 0.3 µg/mL to 50 µg/mL of prostacyclin. In other embodiments, the method comprises exposing the MSC to 0.3 µg/mL to 10 µg/mL of prostacyclin.

In some embodiments, the prostacyclin is treprostinil, a derivative or a salt thereof. In some embodiments, the MSC is exposed to the prostacyclin for at least 24 hours. In other embodiments, the MSC is exposed to the prostacyclin for at least 48 hours.

In some embodiments, the MSC is exposed to the prostacyclin post-expansion.

In some embodiments, the MSC exposed to the prostacyclin has a reduced expression level of TNFα, compared to a control MSC not exposed to the prostacyclin. In other embodiments, the MSC exposed to the prostacyclin has an increased expression level of one or more anti-inflammatory factors selected from the group consisting of IL10, IL13, IDO, iNOS, HLA and TGFβ, compared to a control MSC not exposed to the prostacyclin.

In some embodiments, the MSC exposed to the prostacyclin has an expression level of TNFα that is at least 50% lower than that of a control MSC not exposed to the prostacyclin. In other embodiments, the MSC exposed to the prostacyclin has an expression level at least one of IL10, IL13, IDO, iNOS, HLA and TGFβ that is at least 50% higher than that of a control MSC not exposed to the prostacyclin.

In some embodiments, the one or more components of the MSC is selected from the group consisting of an exosome, a microvesicle, a microRNA, a messenger RNA, a non-coding RNA, a mitochondria, a growth factor, and the combinations thereof.

In some embodiments, the MSC is exposed to treprostinil or a salt thereof having a concentration of 0.3 µg/mL to 10 µg/mL for at least 24 hours.

In some embodiments, the method further comprises isolating an exosome from the culture medium.

Also provided is a composition comprising MSCs exposed to the treprostinil obtained by the method of the present invention. In some embodiments, at least 50% of the MSCs in the composition have an expression level of TNFα that is at least 50% lower than that of a control MSC not exposed to the prostacyclin. In some embodiments, at least 50% of the MSCs in the composition have an expression level of at least one of IL10, IL13, IDO, iNOS, HLA and TGFβ that is at least 50% higher than that of a control MSC not exposed to the prostacyclin.

Also provided is a composition comprising the isolated exosome obtained by the method of the present invention.

In some embodiments, the composition further comprises at least one pharmaceutically acceptable carrier. In some embodiments, such composition further comprises at least one additional therapeutic agent for treating or preventing vasculopathy. In some embodiments, the additional therapeutic agent for can be selected from the group consisting of NO stimulators (e.g., PDE5 inhibitors, such as tadalafil (Adcirca) and Soluble guanylate cyclase stimulators (ProSGC)), Endothelin receptor antagonists, and other prostacyclins.

BRIEF DESCRIPTION OF THE DRAWINGS

Provided as embodiments of this disclosure are drawings which illustrate by exemplification only, and not limitation.

FIG. 3(A) shows that under chronic hypoxia in vivo, circulating levels of TNFα increased 48% compared to control. FIG. 3(B) shows that exposure to treprostinil in vitro at dosage between 83.3 µg/mL and 0.3 µg/mL decreased expression of the pro-inflammatory cytokine TNFα in MSC.

DETAILED DESCRIPTION

Figure 1:
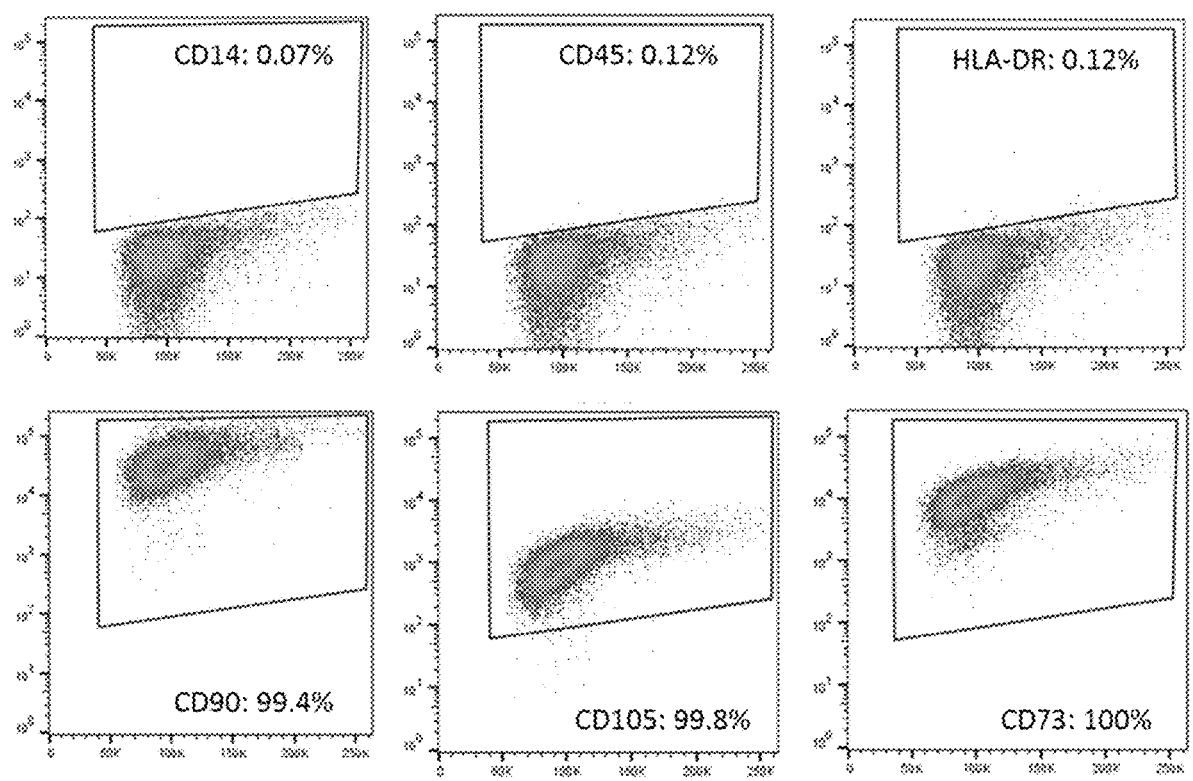
FIG. 1 shows the results of immunophenotype analysis of human bone marrow-derived MSC.

Exposing mesenchymal stem cells (MSC) to relatively low concentrations of a prostacyclin, such as treprostinil, confers an anti-inflammatory phenotype. By exposing MSCs to low concentrations of prostacyclin, the therapeutic potential of the MSCs is enhanced based on their unique gene expression patterns.

MSCs exposed to high concentration of treprostinil, e.g., 250 µg/mL, have enhanced expression of factors that promote angiogenesis in MSCs. However, exposing MSCs to high concentrations of treprostinil also promoted the expression of pro-inflammatory factors, which may not be desirable for PAH treatment in some cases, and also negatively impacted cell viability. The present inventors unexpectedly discovered that low-concentration prostacyclin exposure (e.g., 10 µg/mL of treprostinil), as described herein, decreases the expression of pro-inflammatory factors and increases the expression of anti-inflammatory factors in MSCs. For instance, exposing MSCs to low concentrations of treprostinil significantly decreased expression of TNFα in MSCs exposed to treprostinil and significantly increased the expression of IL-10 and IL-13. Exposing MSC to low concentrations of treprostinil also increased expression of other anti-inflammatory factors, such as IDO, iNOS, HLA, and TGFβ.

MSCs exposed to a prostacyclin as described herein and products of such MSCs can be applied as therapeutic agents. For example, MSCs may be primed by exposing to low concentrations of prostacyclin to become anti-inflammatory prior to administration to a patient. As another example, exosomes from MSCs treated with an appropriate concentration of a prostacyclin, such as treprostinil, can be administered to treat vasculopathy, such as PAH. It is further contemplated that the present invention can be used in a bioprocess step to alter or enhance MSC-secreted signals, such as peptides and vesicles, which may be used as therapeutic agents.

A. Definition

Unless otherwise specified, "a" or "an" means "one or more."

Unless specifically defined otherwise, all technical and scientific terms used herein shall be taken to have the same meaning as commonly understood by one of ordinary skill in the art (e.g., in stem cell biology, cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein, the term "subject" (also referred to herein as a "patient") includes warm-blooded animals, preferably mammals, including humans. In a preferred embodiment, the subject is a primate. In an even more preferred embodiment, the subject is a human.

As used herein the terms "treating", "treat" or "treatment" include eliminating, ameliorating, alleviating, or abating a disease or condition or one or more symptoms thereof, whether or not the disease or condition is considered to be "cured" or "healed" and whether or not all symptoms are resolved. The terms also include reducing or preventing progression of a disease or condition or one or more symptoms thereof, impeding or preventing an underlying mechanism of a disease or condition or one or more symptoms thereof, and achieving any therapeutic and/or prophylactic benefit.

As used herein the terms "preventing", "prevent" or "prevention" include reducing the occurrence of a disease or condition or one or more symptoms thereof relative to an untreated control sample, or delaying the onset of one or more symptoms of the disease or condition relative to the untreated control sample.

As used here, the term "pro-inflammatory factor" refers to a molecule that generally promotes inflammatory processes or is otherwise positively associated with inflammatory processes. Pro-inflammatory factors include, but are not limited to, pro-inflammatory cytokines. Pro-inflammatory factors include tumor necrosis factor alpha (TNFα), Interleukin 1 (IL-1), Interleukin 6 (IL-6), Interleukin 21 (IL-21), Monocyte Chemoattractant Protein-1 (MCP1), and Monocyte Chemoattractant Protein-5 (MCP-5).

As used here, the term "anti-inflammatory factor" refers to a molecule that generally inhibits inflammatory processes or is otherwise positively associated with anti-inflammatory processes. Anti-inflammatory factors include, but are not limited to, anti-inflammatory cytokines. Anti-inflammatory factors include Interleukin 10 (IL 10), Interleukin 13 (IL13), IDO, iNOS, HLA, and TGFβ.

B. Vasculopathy

Vasculopathy includes, but is not limited to, pulmonary hypertension, including pulmonary arterial hypertension (PAH), peripheral vascular disease (PVD), critical limb ischemia (CLI), coronary artery disease, and diabetic vasculopathy.

Although many causes and conditions are found to be associated with PAH, many of them share in common several fundamental pathophysiological features. One important feature among these processes is dysfunction of the endothelium, the internal cellular layer of all vessel walls, which is normally responsible for the production and metabolism of a large array of substances that regulate vessel tone and repair and inhibit clot formation. In the setting of PAH, endothelial dysfunction can lead to excessive production of deleterious substances and impaired production of protective substances. Whether this is the primary event in the development of PAH or part of a downstream cascade remains unknown, but in either case it is an important factor in the progressive vasoconstriction and vascular proliferation that characterize the disease.

The term peripheral vascular disease (PVD) refers to damage, dysfunction or obstruction within peripheral arteries and veins. Peripheral artery disease is the most common form of PVD. Peripheral vascular disease is the most common disease of the arteries and is a very common condition in the United States. It occurs mostly in people older than 50 years. Peripheral vascular disease is a leading cause of disability among people older than 50 years, as well as in those people with diabetes. About 10 million people in the United States have peripheral vascular disease, which translates to about 5% of people older than 50 years. The number of people with the condition is expected to grow as the population ages. Men are slightly more likely than women to have peripheral vascular disease.

Critical limb ischemia (CLI), due to advanced peripheral arterial occlusion, is characterized by reduced blood flow and oxygen delivery at rest, resulting in muscle pain at rest and non-healing skin ulcers or gangrene (Rissanen et al., *Eur. J. Clin. Invest.* 31:651-666 (2001); Dormandy and Rutherford, *J. Vasc. Surg.* 31:S1-S296 (2000)). Critical limb ischemia is estimated to develop in 500 to 1000 per million individuals in one year ("Second European Consensus Document on Chronic Critical Leg Ischemia", *Circulation* 84(4 Suppl.) IV 1-26 (1991)). In patients with critical limb ischemia, amputation, despite its associated morbidity, mortality and functional implications, is often recommended as a solution against disabling symptoms (M. R. Tyrrell et al., *Br. J. Surg.* 80: 177-180 (1993); M. Eneroth et al., Int. Orthop. 16: 383-387 (1992)). There exists no optimal medical therapy for critical limb ischemia (*Circulation* 84(4 Suppl.): IV 1-26 (1991)).

Coronary artery disease (atherosclerosis) is a progressive disease in humans wherein one or more coronary arteries gradually become occluded through the buildup of plaque. The coronary arteries of patients having this disease are often treated by balloon angioplasty or the insertion of stents to prop open the partially occluded arteries. Ultimately, these patients are required to undergo coronary artery bypass surgery at great expense and risk.

C. Mesenchymal Stem Cells (MSCs)

Mesenchymal stem cells (MSCs) are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum. MSC are capable of differentiating into different germ lines such as mesoderm, endoderm, and ectoderm. Thus, MSCs are capable of differentiating into a large number of cell types including, but not limited to, adipose, osseous, cartilaginous, elastic, muscular, and fibrous connective tissues. The specific lineage-commitment and differentiation pathway entered into by MSCs depends upon various influences, including mechanical influences and/or endogenous bioactive factors, such as growth factors, cytokines, and/or local microenvironmental conditions established by host tissues. MSCs are thus non-hematopoietic progenitor cells that divide to yield daughter cells that are either stem cells or are precursor cells that in time will irreversibly differentiate to yield a phenotypic cell. Examples of MSCs include mesenchymal precursor cells (MPCs).

As used herein, the term "stem cell" refers to self-renewing cells that are capable of giving rise to phenotypically and genotypically identical daughters as well as at least one other final cell type (e.g., terminally differentiated cells). The term "stem cells" includes totipotential, pluripotential and multipotential cells, as well as progenitor and/or precursor cells derived from the differentiation thereof.

As used herein, the term "totipotent cell" or "totipotential cell" refers to a cell that is able to form a complete embryo (e.g., a blastocyst).

As used herein, the term "pluripotent cell" or "pluripotential cell" refers to a cell that has complete differentiation versatility, i.e., the capacity to grow into any of the mammalian body's approximately 260 cell types. A pluripotent cell can be self-renewing, and can remain dormant or quiescent within a tissue.

The term "multipotential cell" or "multipotent cell" refers to a cell that is capable of giving rise to any of several mature cell types. As used herein, this phrase encompasses adult or embryonic stem cells and progenitor cells, and multipotential progeny of these cells. Unlike a pluripotent cell, a multipotent cell does not have the capacity to form all of the cell types.

As used herein, the term "progenitor cell" or "precursor cell" refers to a cell that is committed to differentiate into a specific type of cell or to form a specific type of tissue.

In one embodiment, cells are enriched from a sample obtained from a subject. The terms "enriched," "enrichment," and variations thereof are used herein to describe a population of cells in which the proportion of one particular cell type or the proportion of a number of particular cell types is increased when compared with the untreated population.

In one embodiment, the cells used in the present disclosure are TNAP$^+$, STRO-1$^+$, VCAM-1$^+$, THY-1$^+$, STRO-2$^+$, CD45$^+$, CD146$^+$, 3G5$^+$ or any combination thereof Reference to a cell "positive" (also "+") for a given marker means that it may be either a low (lo or dim) or a high (bright, bri) expresser of that marker depending on the degree to which the marker is present on the cell surface, where the terms relate to intensity of fluorescence or other color used in the color sorting process of the cells. The distinction of lo (or dim or dull) and bri will be understood in the context of the marker used on a particular cell population being sorted. Reference to a cell as being "negative" (or "−") for a given marker, does not mean that the marker is not expressed at all by that cell. It means that the marker is expressed at a relatively very low level by that cell, and that it generates a very low signal when detectably labeled. In some embodiments, "negative" can refer to a marker that is not present or present in decreased amounts in cells that have been treated in some fashion, such as exposure to a prostacyclin. In some embodiments, "negative" refers to a marker that is present in at least 50% decreased amounts in cells that have been exposed to prostacyclin when compared to unexposed control sample.

When used herein the term "TNAP" is intended to encompass all isoforms of tissue non-specific alkaline phosphatase. For example, the term encompasses the liver isoform (LAP), the bone isoform (BAP) and the kidney isoform (KAP). In a preferred embodiment, the TNAP is BAP. In a particularly preferred embodiment, TNAP as used herein refers to a molecule that can bind the STRO-3 antibody produced by the hybridoma cell line deposited with ATCC on 19 Dec. 2005 under the provisions of the Budapest Treaty under deposit accession number PTA-7282.

Stem cells useful for the methods can be derived from adult tissue, an embryo, extraembryonic tissue, or a fetus. The term "adult" is used in its broadest sense to include a postnatal subject. In a preferred embodiment, the term "adult" refers to a subject that is postpubertal. The term, "adult" as used herein can also include cord blood taken from a female.

In some aspects, the stem cells can be progeny cells (which can also be referred to as expanded cells). Progeny cells can be produced from the in vitro culture of the stem cells described herein. Expanded cells of the disclosure may have a wide variety of phenotypes depending on the culture conditions (including the number and/or type of stimulatory factors in the culture medium), the number of passages and the like. In certain embodiments, the progeny cells are obtained after about 2, about 3, about 4, about 5, about 6, about 7, about 8, about 9, or about 10 passages from the parental population. However, the progeny cells may be obtained after any number of passages from the parental population. And the progeny cells can be obtained by culturing in a suitable culture medium.

In one embodiment, the progeny cells are obtained by isolating TNAP+cells from bone marrow using magnetic beads labelled with the STRO-3 antibody, and plated in α-MEM supplemented with 20% fetal calf serum, 2 mM L-glutamine and 100 μm L-ascorbate-2-phosphate.

In one embodiment, such expanded cells (at least after 5 passages) can be TNAP-, CC9+, HLA class I+, HLA class II-, CD14-, CD19-; CD3-, CD11a-c-, CD31-, CD86- and/or CD80-. However, it is possible that expression of different markers may vary depending on culture conditions. Also, while cells of these phenotypes may predominate in the expanded cell population, a minor proportion of the cells that do not have this phenotype(s) (for example, a small percentage of the expanded cells may be CC9-) may be present. In some embodiments, these cells will be present in an amount that is 30%, 20%, 15%, 10%, 5%, or 1% or less of the total number of cells present in the expanded cell population. In one preferred embodiment, expanded cells have the capacity to differentiate into different cell types.

In one embodiment, an expanded cell population comprises cells wherein at least 25%, more preferably at least 50%, of the cells are CC9+.

In another embodiment, an expended cell population used in the methods of the disclosure comprises cells wherein at least 40%, more preferably at least 45%, of the cells are STRO-1+.

In a further embodiment, the progeny cells may express markers selected from the group consisting of LFA-3, THY-1, VCAM-1, PECAM-1, P-selectin, L-selectin, 3G5, CD49a/CD49b/CD29, CD49c/CD29, CD49d/CD29, CD29, CD18, CD61, integrin beta, 6-19, thrombomodulin, CD10, CD13, SCF, PDGF-R, EGF-R, IGF1-R, NGF-R, FGF-R, Leptin-R, (STRO-2=Leptin-R), RANKL, STRO-1bright, CD146, and any combination of these markers.

In one embodiment, the progeny cells are Multipotential Expanded MSC Progeny (MEMPs) as described in WO 2006/032092. Methods for preparing enriched populations of MSC from which progeny may be derived are described in WO 01/04268 and WO 2004/085630. In an in vitro context MSCs will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MSC from which progeny are derived may be directly harvested from a tissue source, or alternatively it may be a population that has already been expanded ex vivo.

For example, the progeny may be obtained from a harvested, unexpanded, population of substantially purified MSC, comprising at least about 0.1, 1, 5, 10, 20, 30, 40, 50, 60, 70, 80 or 95% of total cells of the population in which they are present. This level may be achieved, for example, by selecting for cells that are positive for at least one marker selected from the group consisting of TNAP, STRO-$1^{bri}$, 3G5+, VCAM-1, THY-1, CD146 and STRO-2.

The MSC starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon, and skeletal muscle.

MEMPS can be distinguished from freshly harvested MSCs in that they are positive for the marker STRO-1bri and negative for the marker Alkaline phosphatase (ALP). In contrast, freshly isolated MSCs are positive for both STRO-$1^{bri}$ and ALP. In a preferred embodiment of the present disclosure, at least 15%, 20%, 30%, 40%, 50%, 60%, 70%, 80%, 90% or 95% of the administered cells have the phenotype STRO-$1^{bri}$, ALP-. In a further preferred embodiment the MEMPS are positive for one or more of the markers Ki67, CD44 and/or CD49c/CD29, VLA-3, $\alpha3\beta1$. In yet a further preferred embodiment the MEMPs do not exhibit TERT activity and/or are negative for the marker CD18.

In one embodiment, the cells are taken from a patient with vasculopathy, cultured in vitro using standard techniques during at least a portion of the culturing period the cells are exposed to a prostacyclin as described herein, and administered to a patient as an autologous or allogeneic transplant. In an alternative embodiment, cells of one or more of the established human cell lines are used. In another useful embodiment of the disclosure, cells of a non-human animal (or if the patient is not a human, from another species) are used.

The present technology can be practiced using cells from any non-human animal species, including but not limited to non-human primate cells, ungulate, canine, feline, lagomorph, rodent, avian, and fish cells. Primate cells with which the disclosure may be performed include but are not limited to cells of chimpanzees, baboons, cynomolgus monkeys, and any other New or Old World monkeys. Ungulate cells with which the disclosure may be performed include but are not limited to cells of bovines, porcines, ovines, caprines, equines, buffalo and bison. Rodent cells with which the disclosure may be performed include but are not limited to mouse, rat, guinea pig, hamster and gerbil cells. Examples of lagomorph species with which the disclosure may be performed include domesticated rabbits, jack rabbits, hares, cottontails, snowshoe rabbits, and pikas. Chickens (*Gallus gallus*) are an example of an avian species with which the disclosure may be performed.

Cells can be stored before use. Methods and protocols for preserving and storing of eukaryotic cells, and in particular mammalian cells, are well known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present disclosure. In one preferred embodiment, the cells are maintained and stored by using cryo-preservation.

Cells can be obtained using a variety of techniques. For example, a number of cell-sorting techniques by which cells are physically separated by reference to a property associated with the cell-antibody complex, or a label attached to the antibody can be used. This label may be a magnetic particle or a fluorescent molecule. The antibodies may be cross-linked such that they form aggregates of multiple cells, which are separable by their density. Alternatively the antibodies may be attached to a stationary matrix, to which the desired cells adhere.

In a preferred embodiment, an antibody (or other binding agent) that binds TNAP+, STRO-1+, VCAM-1+, THY-1+, STRO-2+, 3G5+, CD45+, CD146+ is used to isolate the cells. More preferably, an antibody (or other binding agent) that binds TNAP+ or STRO-1+ is used to isolate the cells.

Various methods of separating antibody-bound cells from unbound cells are known. For example, the antibody bound to the cell (or an anti-isotype antibody) can be labeled and then the cells separated by a mechanical cell sorter that detects the presence of the label. Fluorescence-activated cell sorters are well known in the art. In one embodiment, anti-TNAP antibodies and/or an STRO-1 antibodies are attached to a solid support. Various solid supports are known to those of skill in the art, including, but not limited to, agarose beads, polystyrene beads, hollow fiber membranes, polymers, and plastic petri dishes. Cells that are bound by the antibody can be removed from the cell suspension by simply physically separating the solid support from the cell suspension.

Super paramagnetic microparticles may be used for cell separations. For example, the microparticles may be coated with anti-TNAP antibodies and/or STRO-1 antibodies. The antibody-tagged, super paramagnetic microparticles may then be incubated with a solution containing the cells of interest. The microparticles bind to the surfaces of the desired stem cells, and these cells can then be collected in a magnetic-field.

In another example, the cell sample is allowed to physically contact, for example, a solid phase-linked anti-TNAP monoclonal antibodies and/or anti-STRO-1 monoclonal antibodies. The solid-phase linking can comprise, for instance, adsorbing the antibodies to a plastic, nitrocellulose, or other surface. The antibodies can also be adsorbed on to the walls of the large pores (sufficiently large to permit flow-through of cells) of a hollow fiber membrane. Alternatively, the antibodies can be covalently linked to a surface or bead, such as Pharmacia Sepharose 6 MB macrobeads. The exact conditions and duration of incubation for the solid phase-linked antibodies with the stem cell containing suspension will depend upon several factors specific to the system employed. The selection of appropriate conditions, however, is well within the skill of the art.

The unbound cells are then eluted or washed away with physiologic buffer after allowing sufficient time for the stem cells to be bound. The unbound cells can be recovered and used for other purposes or discarded after appropriate testing has been done to ensure that the desired separation had been achieved. The bound cells are then separated from the solid phase by any appropriate method, depending mainly upon the nature of the solid phase and the antibody. For example, bound cells can be eluted from a plastic petri dish by vigorous agitation. Alternatively, bound cells can be eluted by enzymatically "nicking" or digesting an enzyme-sensitive "spacer" sequence between the solid phase and the antibody. Spacers bound to agarose beads are commercially available from, for example, Pharmacia.

The eluted, enriched fraction of cells may then be washed with a buffer by centrifugation and said enriched fraction may be cryopreserved in a viable state for later use according to conventional technology, culture expanded and/or introduced into the patient.

D. Culture Media

A "culture medium" as used herein, encompasses (a) both a culture medium that contains the typical components used for culturing a MSC, such as amino acids, glucose, and various salts, with or without the MSC, and (b) a composition isolated from the culture medium, including a composition comprising components released from the MSC during the culturing. The culture medium may contain components that are solid, liquid, gaseous or a mixture of phases and materials. Culture medium components include, but are not limited to, agar, agarose, gelatin and collagen matrices. "Culture medium" includes material that is intended for use in a cell culture, even if it has not yet been contacted with cells. For example, a nutrient rich liquid prepared for bacterial culture can be a culture medium.

A "culture medium that has been in contact with MSC" refers to a culture medium that has been in contact with a MSC (e.g., for the purpose of culturing the MSC) and thus comprises components released from the MSC. Non-limiting examples of such released components include exosomes or other microvesicles, which can comprise messenger RNA, non-coding RNA, microRNAs, mitochondria, growth factors, or other types of bioactive agents.

E. Microvesicles and Exosomes

MSCs can release compounds and other materials into the extracellular environment during growth or differentiation. In some aspects, such materials include extracellular vesicles. Extracellular vesicles comprise fragments of plasma membrane derived from various cell types. Typically, extracellular vesicles have a diameter (or largest dimension where the particle is not spheroid) of between about 10 nm to about 5000 nm (e.g., between about 50 nm and 1500 nm, between about 75 nm and 1500 nm, between about 75 nm and 1250 nm, between about 50 nm and 1250 nm, between about 30 nm and 1000 nm, between about 50 nm and 1000 nm, between about 100 nm and 1000 nm, between about 50 nm and 750 nm, etc.). Alternative names for extracellular vesicles include, but are not limited to, microvesicles, exosomes, ectosomses, membrane particles, exosome-like particles, and apoptotic vesicles. Unless otherwise specified, any particular type of extracellular vesicles or combination of types of extracellular vesicles can be used according to this disclosure. For example, an ectosome, exosome-like particle, or combinations thereof can be used in place of an exosome.

Exosomes are vesicles derived from the multivesicular body sorting pathway. Recent studies show that exosomes are bioactive vesicles useful for intercellular communication and facilitation of the immunoregulatory process. MSC exosomes can contain 20S proteasomes and numerous RNAs (messenger RNA, non-coding RNA, microRNA). In some embodiments, the exosomes are between 30 nm and 200 nm in diameter or 20 nm to 50 nm in diameter. In some embodiments, the exosomes have a density in sucrose of 1.10 to 1.19 g/mL, sedimented at 100,000 g. In some embodiments, the exosome's membrane can comprise sphingomyelin, ceramide, lipid rafts, and exposed phosphatidylserine.

One aspect of the present invention provides a composition comprising exosomes isolated from MSCs that have been exposed to a prostacyclin, such as treprostinil. Such exosomes are suitable for the treatment of vasculopathy, including pulmonary hypertension. Generally any suitable method for purifying and/or enriching exosomes can be used, such as methods comprising magnetic particles, filtration, dialysis, ultracentrifugation, ExoQuick™ (Systems Biosciences, CA, USA), and/or chromatography.

In some embodiments, exosomes are isolated by centrifugation and/or ultracentrifugation. The protocol is described in, for example, Thery et al. *Current Protocols in Cell Biol.* (2006) 3.22. In some embodiments, exosomes are isolated by a single step size exclusion chromatography. The protocol is described in, for example, Boing et al. *Journal of Extracellular Vesicles* (2014) 3:23430.

In addition to exosomes, MSC also release other bioactive molecules/vesicles. Such molecules and vesicles include, without limitation, mitochondria and growth factors. Method of preparing culture media that contain such molecules and vesicles released from MSC and further isolating particular molecules and vesicles are known in the art. See Hu et al., *Frontiers in Genetics,* 2:56, 1-9 (2012).

F. Prostacyclin

The term "prostacyclin" used herein explicitly comprises any prostaglandin $I_2$ ($PGI_2$), any prostacyclin analogues, and any $PGI_2$ receptor agonists. Non-limiting examples of prostacyclins suitable for the present technology include epoprostenol, treprostinil, iloprost, and selexipag, as well as any salts thereof, including treprostinil sodium. In one aspect, the prostacyclin is treprostinil, a derivative, a pharmaceutically acceptable salt, or an ester thereof.

G. Exposing MSC to Prostacyclin

In some embodiments, prior to administration, an MSC or a culture medium that has been in contact with MSC can be exposed to prostacyclin. Accordingly, also provided, in some embodiments, is a method for preparing an MSC or a culture medium that has been in contact with MSC, or an exosome derived from the MSC for in vivo delivery, comprising contacting the MSC or MSC-conditioned culture medium with a prostacyclin. Yet another embodiment provides a MSC or MSC-conditioned culture medium obtained by such a method.

Exposure of a cell or a medium with a chemical compound encompasses known techniques. In one aspect, the prostacyclin can be added to and co-incubated with a culture medium that contains a MSC. Optionally, however, such co-incubation can further involve the addition of a growth factor (e.g., VEGF and Angiopoietin-1 or -2, platelet-derived growth factor) and/or hypoxia.

MSCs or a culture medium that has been in contact with MSCs can be exposed to prostacyclin in various ways. For example, MSCs can be exposed to prostacyclin ex vivo during the expansion of MSCs. MSCs can also be exposed to prostacyclin post-expansion. According to one embodiment of the present disclosure, MSCs can be prepared from the subject's own blood or bone marrow. In that case, MSCs can be exposed to prostacyclin before they are isolated from the subject and/or the MSCs can be exposed to prostacyclin after isolation.

In some embodiments, a MSC is exposed to prostacyclin ex vivo for at least about 12 hours, at least about 18 hours, at least about 24 hours, at least about 30 hours, at least about 36 hours, about 42 hours, at least about 48 hours, or at least about 54 hours.

In some embodiments, a MSC is exposed to prostacyclin ex vivo at concentration of about 0.001 µg/mL to about 100 µg/mL, about 0.001 µg/mL to about 50 µg/mL, about 0.01 µg/mL to about 20 µg/mL, about 0.1 µg/mL to about 10 µg/mL, or about 1 µg/mL to about 5 µg/mL. In some embodiments, a MSC is treated with prostacyclin at concentration of about 0.3 µg/mL to about 83.3 µg/mL, or about 0.3 µg/mL to about 10 µg/mL. In some embodiments, a MSC is exposed to prostacyclin at concentration of about 100 µg/mL, 75 µg/mL, 50 µg/mL, 25 µg/mL, 10 µg/mL, 5 µg/mL, 2.5 µg/mL, 1 µg/mL, 0.5 µg/mL, 0.25 µg/mL, 0.1 µg/mL, 0.05 µg/mL, or about 0.01 µg/mL. The concentration of prostacyclin refers to the concentration of prostacyclin in the MSC culture medium.

In some embodiments, MSC exposed to prostacyclin has an expression level of a pro-inflammatory factor or pro-inflammatory cytokine that is at least 30%, at least 40%, at least 50%, at least 1 fold, at least 1.5 fold, at least 2 fold, at least 3 fold, at least 4 fold, or at least 5 fold lower than the expression level of a control MSC not exposed to the prostacyclin. In some embodiments, the pro-inflammatory factor is TNF-a. In some embodiments, the expression level of more than one pro-inflammatory factors are decreased by the prostacyclin exposure.

In some embodiments, MSC exposed to prostacyclin has an expression level of an anti-inflammatory factor or anti-inflammatory cytokine that is at least 30%, at least 40%, at least 50%, at least 1 fold, at least 1.5 fold, at least 2 fold, at least 3 fold, at least 4 fold, or at least 5 fold, at least 6 fold, at least 7 fold, at least 8 fold, at least 9 fold, or at least 10 fold higher than the expression level of a control MSC not exposed to the prostacyclin. In some embodiments, the expression level of more than one anti-inflammatory factors are increased by the prostacyclin exposure. In some embodiments, the anti-inflammatory factor is selected from the group consisting of IL 10, IL13, IDO, iNOS, HLA, TGFβ, and a combination thereof.

In some embodiments, exposure of MSC to prostacyclin simultaneously reduces the expression level of one or more pro-inflammatory factors, and increases the expression level of one or more anti-inflammatory factors. In some embodiments, exposure of MSC to prostacyclin simultaneously reduces the expression level of TNF-α and/or IL-4, and increases the expression level of one or more anti-inflammatory factors selected from the group consisting of IL 10, IL13, IDO, iNOS, HLA, and TGFβ.

H. Pharmaceutical Compositions

In one aspect, the present disclosure provides a pharmaceutical composition comprising a therapeutically effective amount of a MSC, or a part of a culture medium that has been in contact with the MSC comprising one or more components of the MSC, or exosomes derived from the MSC.

In some embodiments, the pharmaceutical composition comprises MSCs that have been exposed to treprostinil, such as those described herein. In some embodiments, at least 30%, at least 40%, at least 50%, at least 60%, at least 70%, at least 80%, at least 90%, at least 95%, at least 98%, or at least 99% of all MSCs in the composition have an expression level of TNFα that is at least 50% lower than that of a control MSC not exposed to the prostacyclin. In some embodiments, at least 30%, at least 40%, at least 50%, at least 60%, at least 70%, at least 80%, at least 90%, at least 95%, at least 98%, or at least 99% of all MSCs in the composition have an expression level of at least one of IL10, IL13, DO, iNOS, HLA and TGFβ that is at least 50% higher than that of a control MSC not exposed to the prostacyclin.

In some embodiments, the pharmaceutical composition further comprises at least one pharmaceutically-acceptable carrier. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically-acceptable carrier" as used herein means a pharmaceutically-acceptable material, composition or vehicle, such as a liquid or solid filler, diluent, excipient, or solvent encapsulating material.

Pharmaceutically acceptable carriers include saline, aqueous buffer solutions, solvents and/or dispersion media. The use of such carriers are well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Some examples of materials and solutions which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The pharmaceutical compositions useful for the methods of the disclosure may comprise a polymeric carrier or extracellular matrix.

A variety of biological or synthetic solid matrix materials (e.g.,, solid support matrices, biological adhesives or dressings, and biological/medical scaffolds) are suitable for use in this disclosure. The matrix material is preferably medically acceptable for use in in vivo applications. Non-limiting examples of such medically acceptable and/or biologically or physiologically acceptable or compatible materials include, but are not limited to, solid matrix materials that are absorbable and/or non-absorbable, such as small intestine submucosa (SIS), e.g., porcine-derived (and other SIS sources); crosslinked or non-crosslinked alginate, hydrocolloid, foams, collagen gel, collagen sponge, polyglycolic acid (PGA) mesh, polyglactin (PGL) mesh, fleeces, foam dressing, bioadhesives (e.g., fibrin glue and fibrin gel) and dead de-epidermized skin equivalents in one or more layers Suitable polymeric carriers include porous meshes or sponges formed of synthetic or natural polymers, as well as polymer solutions. One form of matrix is a polymeric mesh or sponge; the other is a polymeric hydrogel. Natural polymers that can be used include proteins such as collagen, albumin, and fibrin; and polysaccharides such as alginate and polymers of hyaluronic acid. Synthetic polymers include both biodegradable and non-biodegradable polymers. Examples of biodegradable polymers include polymers of hydroxy acids such as polylactic acid (PLA), polyglycolic acid (PGA), and polylactic acid-glycolic acid (PLGA), polyorthoesters, polyanhydrides, polyphosphazenes, and combinations thereof. Non-biodegradable polymers include polyacrylates, polymethacrylates, ethylene vinyl acetate, and polyvinyl alcohols.

Polymers that can form ionic or covalently crosslinked hydrogels which are malleable are used to encapsulate cells. A hydrogel is a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

In some embodiments, the pharmaceutical composition can comprise at least one additional therapeutic agent. For example, the composition may contain an analgesic to aid in treating inflammation or pain, or an anti-infective agent to prevent infection of the site treated with the composition. More specifically, non-limiting examples of useful therapeutic agents include the following therapeutic categories: analgesics, such as nonsteroidal anti-inflammatory drugs, opiate agonists and salicylates; anti-infective agents, such as antihelmintics, antianaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, anti-inflammatory agents, corticosteroid anti-inflammatory agents, antipruritics/local anesthetics, topical anti-infectives, antifungal topical anti-infectives, antiviral topical anti-infectives; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, gastrointestinal anti-inflammatory agents, gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agent's, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hormones and hormone modifiers, such as abortifacients, adrenal agents, corticosteroid adrenal agents, androgens, anti-androgens, immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, minerals; and vitamins, such as vitamin A, vitamin B, vitamin C, vitamin D, vitamin E, and vitamin K.

Compositions useful for the methods of the present disclosure may include cell culture components, e.g., culture media including amino acids, metals, coenzyme factors, as well as small populations of other cells, e.g., some of which may arise by subsequent differentiation of the stem cells.

Compositions useful for the methods of the present disclosure may be prepared, for example, by sedimenting out the subject cells from the culture medium and re-suspending them in the desired solution or material. The cells may be sedimented and/or changed out of the culture medium, for example, by centrifugation, filtration, ultrafiltration, etc.

I. Administration

In some embodiments, the pharmaceutical composition can be administered alone or co-administered with prostacyclin. In some embodiments, the pharmaceutical composition and prostacyclin are administered concurrently. In other embodiments, the prostacyclin and the composition are administered separately. When administered separately, the prostacyclin can be administered prior to, or following the administration of the MSC composition.

The skilled artisan can readily determine the amount of cells and optional carrier(s) in compositions and to be administered in methods of the disclosure. In an embodiment, any additives (in addition to the active cell(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Compositions useful for the methods of the present disclosure can be administered via, inter alia, localized injection, including catheter administration, systemic injection, localized injection, intravenous injection, intrauterine injection or parenteral administration. When administering a therapeutic composition described herein (e.g., a pharmaceutical composition), it will generally be formulated in a unit dosage injectable form (solution, suspension, emulsion).

According to one embodiment of the present disclosure, the compositions can be co-administered with at least one other medicine for vasculopathy. For example, the pharmaceutical compositions can be co-administered with a prostaglandin $I_2$ ($PGI_2$), prostacyclin analogues, phosphodiesterase-5 (PDE-5) inhibitor, endothelin receptor antagonist (ETRA), tyrosine kinase inhibitors, or soluble guanylate cyclase stimulator.

According to one embodiment, the method for treating vasculopathy further comprises reducing thrombosis in pulmonary arteries, reducing inflammation in pulmonary arteries, reducing the proliferation of intimal smooth muscle in pulmonary arteries, reducing the formation of plexiform lesions in pulmonary arteries, increasing the amount of nitric oxide in pulmonary arteries, increasing the amount of PGI2 in pulmonary arteries, reducing the level of Endothelin-1 in pulmonary arteries, reducing the amount of growth factors in pulmonary arteries, or promoting proper endothelial morphology in pulmonary arteries.

Although the foregoing refers to particular preferred embodiments, it will be understood that the present disclosure is not so limited. It will occur to those of ordinary skill in the art that various modifications may be made to the disclosed embodiments and that such modifications are intended to be within the scope of the present disclosure.

All of the publications, patent applications and patents cited in this specification are incorporated herein by reference in their entirety. To the extent that these publications, patent applications and patents contain definitions that differ from the definition provided herein or uses terms or phrases in a different manner, the definitions and usages in this specification control.

EXAMPLES

The following examples are intended to provide those of ordinary skill in the art with a complete disclosure and description of how to make and use the methods and compositions described herein, and are not intended to be limiting.

Example 1

MSC Phenotype and Morphology Studies

This example verifies the phenotype of the MSC cells exposed to treprostinil and determines an optimal dose range for treprostinil exposure without producing cytotoxic effects on the MSC cell.

A single vial of human bone marrow-derived MSC was expanded and seeded using standard growth medium. At 95-99% confluency, cells were thoroughly washed with phosphate-buffered saline (PBS) and exposed to media containing treprostinil at doses ranging from 250 µg/mL to 0.004 µg/mL. After 48 hours of culture, cells were photographed and assessed for treatment-induced changes in morphology.

Flow cytometry analysis (FIG. 1) demonstrated that the bone marrow MSCs used in this study were negative or low for CD34, CD45, and HLA-DR and positive for MSC markers CD73, CD105, and CD90. Definition of MSC was established by the International Society for Cellular Therapy (Dominici et al., *Cytotherapy* 8(4):315-7, 2006).

Images of MSCs exposed to different concentrations of treprostinil (FIG. 2) showed that MSCs appear rounded up and detached at the highest Tre dose (250 µg/mL), which is indicative of a cytotoxic effect of treprostinil on MSC. On the other hand, treprostinil at doses 83.3 µg/mL or lower did not cause morphological changes associated with cell death.

Figure 2:
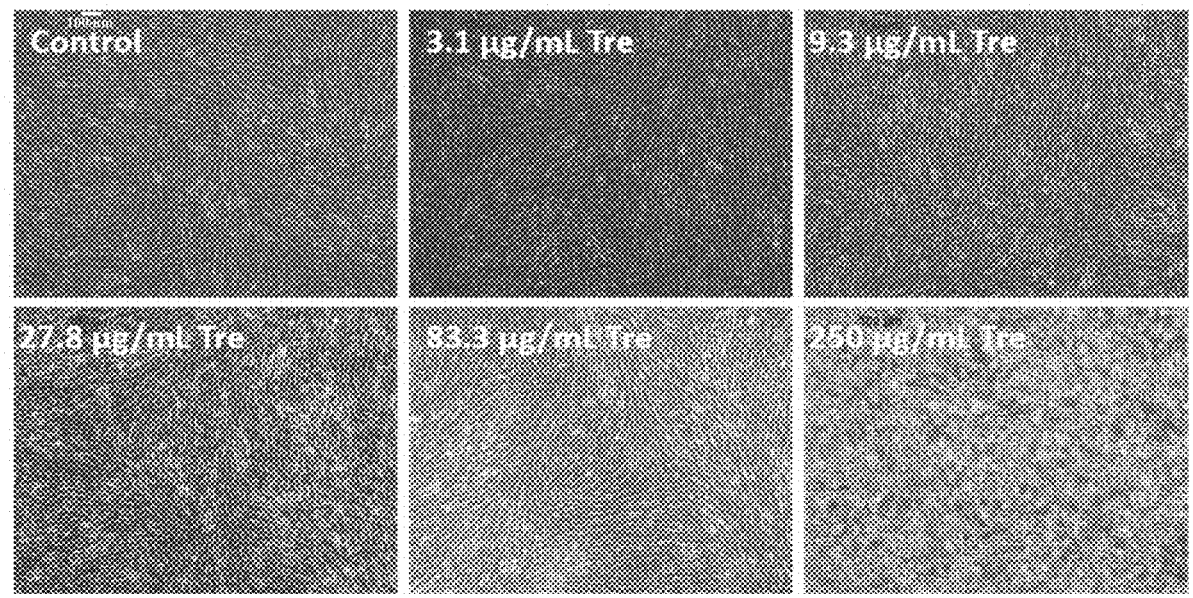
FIG. 2 provides representative images of MSC exposed in culture to different concentrations of treprostinil for 48 hours.

This example demonstrates that high doses of treprostinil negatively impact MSC cell viability while doses of treprostinil lower than 83.3 µg/mL did not cause this cytotoxic effect (FIG. 2). Subsequent studies included a range of low treprostinil doses to avoid cytotoxic effects.

Example 2

Treprostinil Effects on Pro- and Anti-Inflammatory Cytokines

This example examined the effect of treprostinil on the production of pro- and anti-inflammatory cytokines in MSC.

Cells exposed to treprostinil ranging from 250 µg/mL-0.004 µg/mL as described in Example 1 were harvested. RNA of the cells was extracted and then analyzed for pro- and anti-inflammatory cytokines. Cytokines, or small proteins involved in both internal and secreted cell signaling, have been identified to play a role in the inflammatory pathogenesis of PAH (Groth et al., *Respiratory Research*, 15:47 (2014)).

Figure 3A:
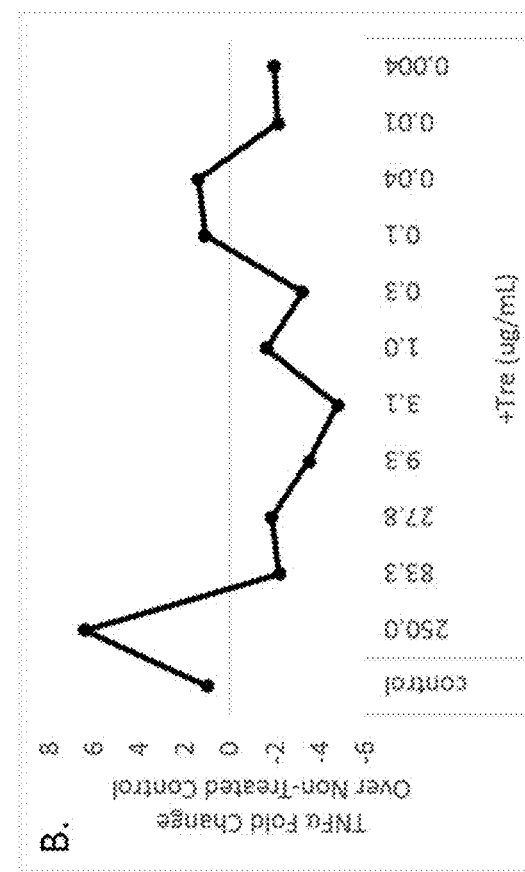
FIGS. 3A and 3B shows effects of exposure to treprostinil on MSC inflammation.
Figure 3B:
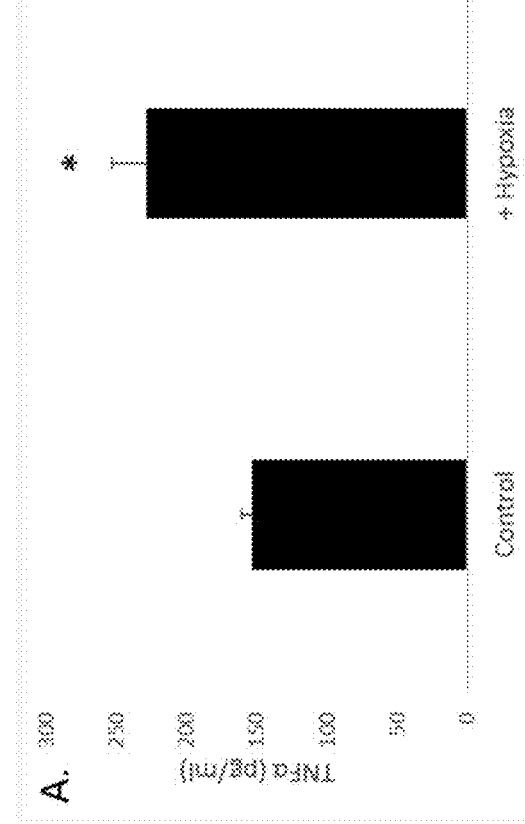

Under chronic hypoxia in vivo, circulating levels of TNFα increased 48% compared to control (FIGS. 3A and 3B). In vitro treprostinil exposure at doses between 83.3 and 0.3 µg/ml decreased the expression level of the pro-inflammatory cytokine TNFα in MSC.

Figure 4:
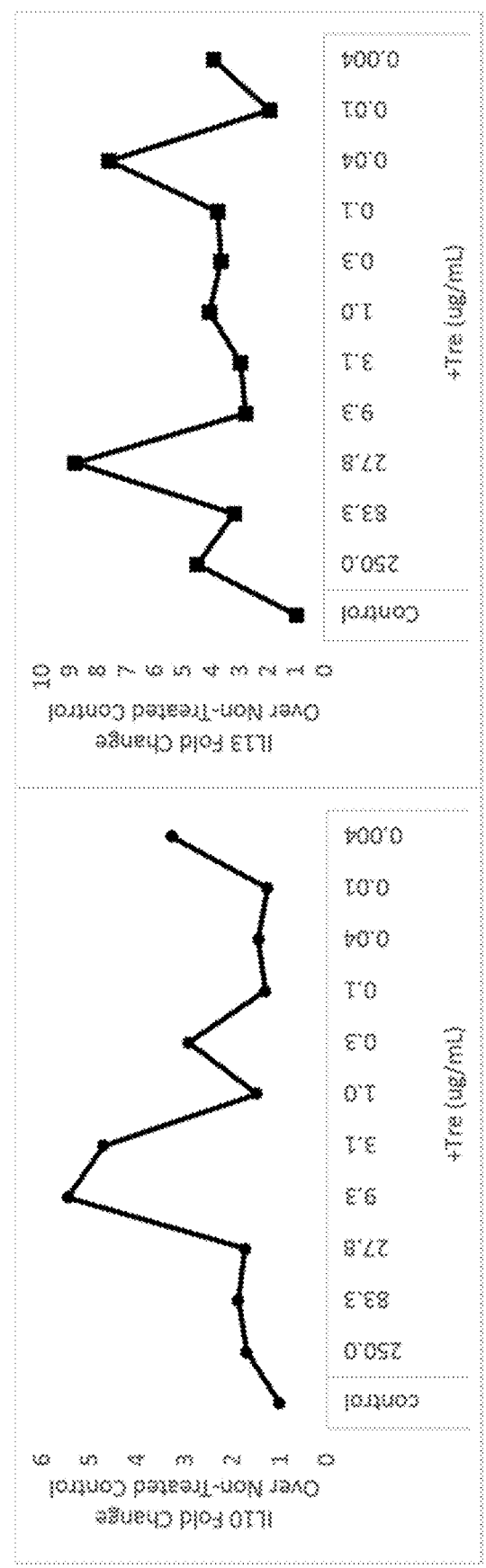
FIG. 4 illustrates that treprostinil exposure increased expression levels of anti-inflammatory factors IL 10 and IL 13.

Exposure of MSC to increasing doses of treprostinil revealed an increase in IL10 and IL13 signaling over control (FIG. 4).

In hypoxia-induced PAH mice, a 48% increase in circulating levels of TNFα was observed (FIG. 3A). Interestingly, exposure with treprostinil of 0.3 µg/mL to 83.3 µg/mL lowered the expression of TNFα by up to 4.7 fold compared to the control (FIG. 3B). Further analysis revealed that the same treprostinil dose range increased the expression level of anti-inflammatory cytokines IL10 and IL13. Specifically, the expression of IL10 in MSC increased by 5.4 fold when exposed to 9.3 µg/mL treprostinil. The expression of IL13 in MSC increased by 8.8 fold when exposed to 27.8 µg/mL treprostinil (FIG. 4). These data indicates that the anti-inflammatory potential of MSCs was induced by low-concentration treprostinil exposure.

Example 3

Treprostinil Effects on Production of Immunosuppressive Factors

This example examined the effect of treprostinil on the MSC production of several immunosuppressive factors.

RNA from MSCs exposed to treprostinil of from 250 µg/mL to 0.004 µg/mL was re-analyzed for several other anti-inflammatory factors. Genes that have been shown to play a specific role in the immunosuppressive properties of MSC including IDOL iNOS, HLA and TGFβ (Hoogduijn et al., *International Immunopharmacology*, 1496-1500(2010)) were assessed.

Figure 5:
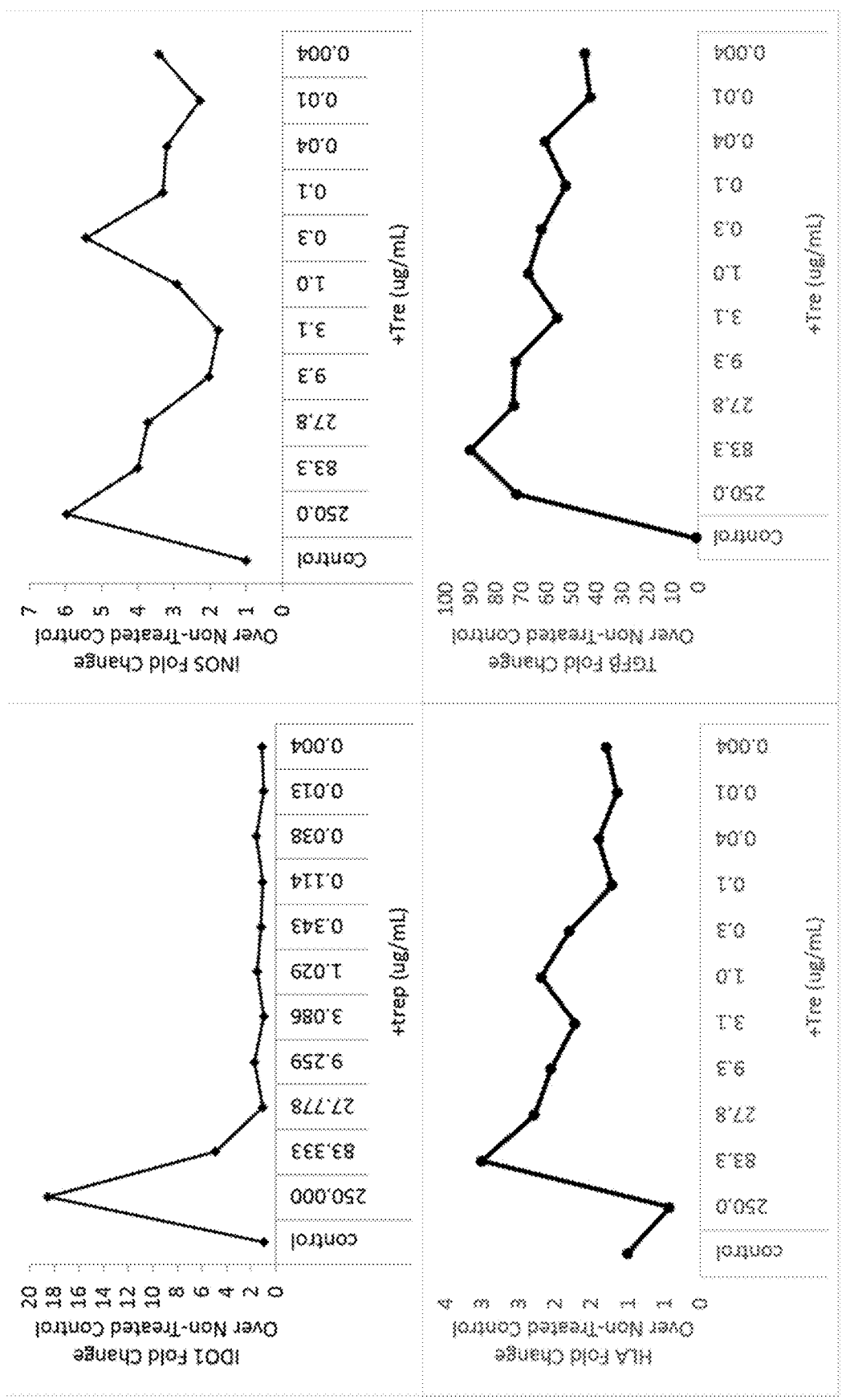
FIG. 5 illustrates that treprostinil exposure increased expression levels of anti-inflammatory factors IDO1, iNOS, HLA, and TGFβ.

MSC exposed to increasing doses of treprostinil revealed a robust increase in anti-inflammatory factors IDO1, iNOS, HLA and TGFβ over control (FIG. 5).

Figure 6:
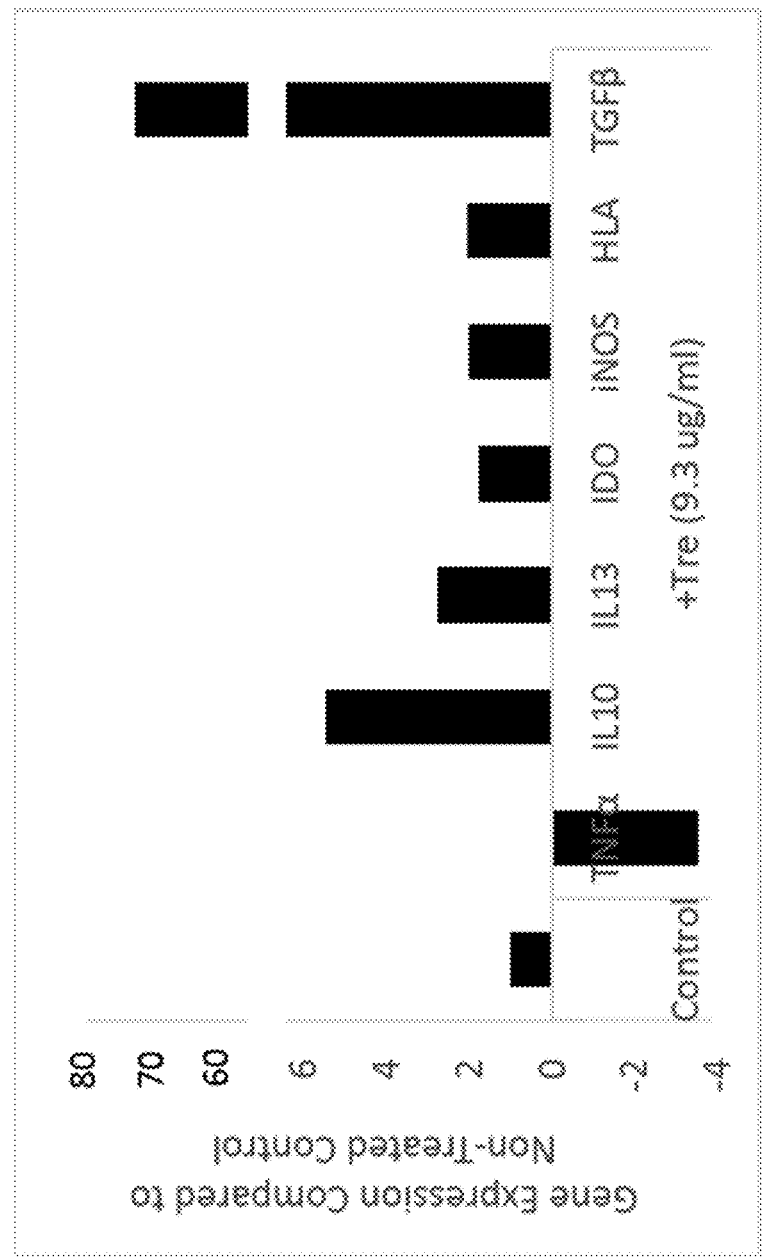
FIG. 6 shows a summary of the immunomodulatory effect of exposure to treprostinil of 9.3 µg/mL.

Exposure of MSC to 9.3 µg/mL treprostinil decreased TNFα (pro-inflammatory cytokine) and increased IL10, IL13, IDO, iNOS, HLA and TGFβ (anti-inflammatory factors) over unexposed control (FIG. 6).

This example demonstrates that MSC exposed to increasing doses of treprostinil revealed a robust increase in anti-inflammatory factors IDO1, iNOS, HLA and TGFβ over control (FIG. 5). This gene expression profile, coupled with the cytokine profile in Example 2 indicate an alteration in MSC gene expression pattern after 48 hours of exposure to multiple doses of treprostinil in vitro. Exposure to 9.3 µg/mL treprostinil decreased the pro-inflammatory cytokine TNFα and increased several anti-inflammatory factors including IL10, IL13, IDO, iNOS, HLA and TGFβ (FIG. 6). These data suggest treprostinil-exposed MSC could serve as an immunomodulatory factor in the treatment of disease.

Figure 7:
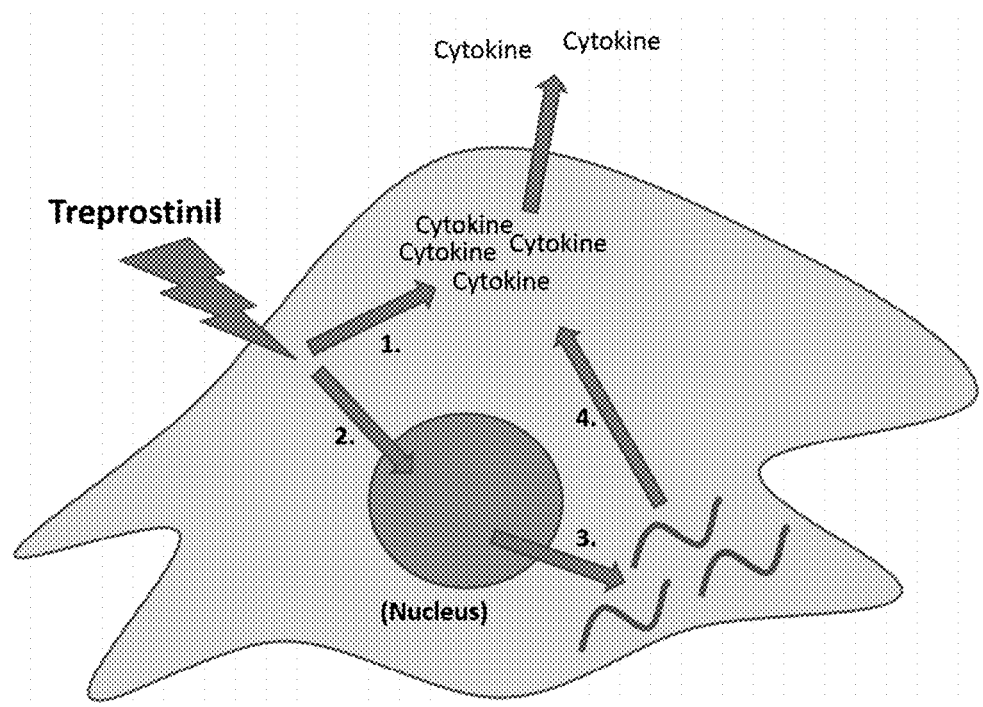
FIG. 7 shows a potential model for the immunomodulatory effect of exposure to treprostinil on MSC. In particular, exposure to treprostinil decreased pro-inflammatory cytokine expression and increased anti-inflammatory cytokine expression through intracellular (1) or nuclear signaling (2, 3, 4).

A proposed model for the immunomodulatory effect of treprostinil exposure is illustrated in FIG. 7. In particular, treprostinil exposure of MSC decreased pro-inflammatory and increased anti-inflammatory cytokines through intracellular (1) or nuclear signaling (2, 3, 4). Further analysis revealed genetic reprogramming of treprostinil-exposed MSC toward an anti-inflammatory state through nuclear signaling (2) measured by changes in RNA expression (3).

The invention claimed is:

1. A method of treating or preventing vasculopathy, comprising
   (a) selecting a mesenchymal stem cell (MSC) following exposure of the MSC to 0.3 µg/mL to 10 µg/mL of a prostacyclin during ex vivo culture having an at least 30% higher expression level of one or more anti-inflammatory factors and a reduced expression level of one or more pro-inflammatory factors as compared to a control MSC not exposed to the prostacyclin,
   (b) administering to a subject in need thereof a composition comprising (i) a part of a culture medium that has been in contact with and comprises one or more components of the MSC selected in step (a), or (ii) an exosome derived from the MSC_selected in step (a).

2. The method of claim 1, wherein the prostacyclin is treprostinil, a derivative or a salt thereof.

3. The method of claim 1, wherein the MSC is exposed to the prostacyclin for at least 24 hours.

4. The method of claim 1, wherein the MSC is exposed to the prostacyclin for at least 48 hours.

5. The method of claim 1, wherein the vasculopathy is selected from the group consisting of pulmonary arterial hypertension (PAH), peripheral vascular disease (PVD), critical limb ischemia (CLI), coronary artery disease and diabetic vasculopathy.

6. The method of claim 1, wherein the vasculopathy is pulmonary arterial hypertension (PAH).

7. The method of claim 1, wherein the MSC is exposed to the prostacyclin post-expansion.

8. The method of claim 1, wherein the MSC exposed to the prostacyclin has a reduced expression level of tumor necrosis factor alpha (TNFα), compared to a control MSC not exposed to the prostacyclin.

9. The method of claim 1, wherein the MSC exposed to the prostacyclin has an increased expression level of one or more anti-inflammatory factors selected from the group consisting of IL10, IL13, IDO, iNOS, HLA and TGFβ, compared to a control MSC not exposed to the prostacyclin.

10. The method of claim 1, wherein the MSC exposed to the prostacyclin has an expression level of TNFβ that is at least 50% lower than that of a control MSC not exposed to the prostacyclin.

11. The method of claim 1, wherein the MSC exposed to the prostacyclin has an expression level at least one of IL10, IL13, IDO, iNOS, HLA and TGFα that is at least 50% higher than that of a control MSC not exposed to the prostacyclin.

12. The method of claim 1, comprising administering to the subject a composition comprising a part of a culture medium that has been in contact with the MSC and comprises one or more components of the MSC, wherein the MSC has been exposed to treprostinil ex vivo or a salt thereof at a concentration of 0.3 to 10 µg/mL for at least 24 hours, and wherein the one or more components of the MSC are selected from the group consisting of an exosome, a microvesicle, a microRNA, a messenger RNA, a non-coding RNA, a mitochondria, a growth factor, and the combinations thereof.

13. The method of claim 1, comprising administering to a subject in need thereof a composition comprising an exosome derived from the MSC, wherein the MSC has been exposed to treprostinil ex vivo or a salt thereof at a concentration of 0.3 to 10 µg/mL for at least 24 hours.

14. The method of claim 1, wherein the MSC is exposed to treprostinil or a salt thereof having a concentration of 0.3 µg/mL to 10 µg/mL for at least 24 hours.

15. The method of claim 1, wherein the part of the culture medium or the exosome has been isolated from the culture medium in which the MSC has been exposed to the prostacyclin.

16. The method of claim 15, wherein the part of the culture medium or the exosome is isolated by using purification methods comprising magnetic particles, filtration, dialysis, ultracentrifugation, and/or size-exclusion chromatography.

\* \* \* \* \*

UNITED STATES PATENT AND TRADEMARK OFFICE
CERTIFICATE OF CORRECTION

| | | |
|---|---|---|
| PATENT NO. | : 11,571,444 B2 | Page 1 of 1 |
| APPLICATION NO. | : 15/790666 | |
| DATED | : February 7, 2023 | |
| INVENTOR(S) | : Roger Marquez Ilagan, Sarah Hogan and John B. Cheadle | |

It is certified that error appears in the above-identified patent and that said Letters Patent is hereby corrected as shown below:

In the Claims

Column 20, Claim 10, Line 36, "TNFβ" should be --TNFα--.

Column 20, Claim 11, Line 41, "TNFα" should be --TNFβ--.

Signed and Sealed this
Sixth Day of August, 2024

*Katherine Kelly Vidal*

Katherine Kelly Vidal
*Director of the United States Patent and Trademark Office*